(12) United States Patent
Govari et al.

(10) Patent No.: US 10,456,196 B2
(45) Date of Patent: Oct. 29, 2019

(54) MONITORING AND TRACKING BIPOLAR ABLATION

(75) Inventors: Assaf Govari, Haifa (IL); Andres Claudio Altmann, Haifa (IL); Yaron Ephrath, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1191 days.

(21) Appl. No.: 13/326,456

(22) Filed: Dec. 15, 2011

(65) Prior Publication Data
US 2013/0158545 A1 Jun. 20, 2013

(51) Int. Cl.
*A61B 18/14* (2006.01)

(52) U.S. Cl.
CPC .................. *A61B 18/1492* (2013.01)

(58) Field of Classification Search
CPC ...... A61B 2018/00577; A61B 18/1492; A61B 2018/00357; A61B 5/0422; A61B 5/062; A61B 5/0538
USPC .......................................................... 606/41
See application file for complete search history.

(56) References Cited

U.S. PATENT DOCUMENTS

| | | | | |
|---|---|---|---|---|
| 5,404,638 A * | 4/1995 | Imran | ............................ | 29/884 |
| 5,579,764 A * | 12/1996 | Goldreyer | ............ | A61B 5/0422 600/374 |
| 5,860,920 A * | 1/1999 | McGee et al. | ................. | 600/374 |
| 5,954,665 A * | 9/1999 | Ben-Haim | ..................... | 600/515 |
| 6,226,542 B1 | 5/2001 | Reisfeld | | |
| 6,301,496 B1 | 10/2001 | Reisfeld | | |
| 6,663,627 B2 * | 12/2003 | Francischelli | ........... | A61B 5/04 606/34 |
| 6,814,733 B2 | 11/2004 | Schwartz et al. | | |
| 6,892,091 B1 | 5/2005 | Ben-Haim et al. | | |
| 6,997,924 B2 | 2/2006 | Schwartz et al. | | |
| 7,156,816 B2 | 1/2007 | Schwartz et al. | | |
| 7,306,593 B2 | 12/2007 | Keidar et al. | | |
| 7,536,218 B2 | 5/2009 | Govari et al. | | |
| 8,359,092 B2 | 1/2013 | Hayam et al. | | |

(Continued)

FOREIGN PATENT DOCUMENTS

| | | |
|---|---|---|
| EP | 0 499 491 A2 | 8/1992 |
| JP | 2005-199072 A | 7/2005 |
| JP | 2009-183687 A | 8/2009 |

OTHER PUBLICATIONS

Wikipedia "Near field electromagnetic ranging" http://en.wikipedia.org/wiki/Near-field_electromagnetic_ranging, Accessed Aug. 11, 2014, last modified Oct. 26, 2013.*

(Continued)

*Primary Examiner* — Carl H Layno
*Assistant Examiner* — Erin M Plateski
(74) *Attorney, Agent, or Firm* — Vincent J. Serrao

(57) ABSTRACT

Methods and systems treat abnormal cardiac electrical activity employing a probe having first and second ablation electrodes disposed on a distal portion of the probe and a sensing electrode disposed between the first and second ablation electrodes, bringing the probe into contact with cardiac tissue, and applying energy through the first and second ablation electrodes to ablate target tissue along an ablation path, monitoring cardiac electrical activity using the sensing electrode to detect the cardiac electrical activity. After making an observation that the cardiac electrical activity is no longer detectable by the sensing electrode, energy application is terminated.

9 Claims, 2 Drawing Sheets

(56) References Cited

U.S. PATENT DOCUMENTS

| | | | |
|---|---|---|---|
| 2001/0008967 A1* | 7/2001 | Sherman | 606/34 |
| 2002/0087151 A1 | 7/2002 | Mody et al. | |
| 2002/0151807 A1* | 10/2002 | Goldin | 600/509 |
| 2003/0199862 A1* | 10/2003 | Simpson et al. | 606/34 |
| 2004/0006333 A1 | 1/2004 | Arnold et al. | |
| 2007/0016007 A1* | 1/2007 | Govari et al. | 600/424 |
| 2008/0275440 A1 | 11/2008 | Kratoska et al. | |
| 2009/0264778 A1* | 10/2009 | Markowitz et al. | 600/508 |
| 2010/0004661 A1 | 1/2010 | Verin et al. | |
| 2010/0125269 A1* | 5/2010 | Emmons et al. | 606/33 |
| 2010/0274238 A1* | 10/2010 | Klimovitch | 606/33 |
| 2010/0305562 A1* | 12/2010 | Winkler | A61B 18/1482 606/33 |
| 2010/0312096 A1* | 12/2010 | Guttman et al. | 600/411 |
| 2011/0125150 A1* | 5/2011 | Deno | A61B 18/1492 606/34 |

OTHER PUBLICATIONS

Bevelacqua "Field Regions", [http://www.antenna-theory.com/basics/fieldRegions.php, captured Apr. 28, 2010].*
U.S. Appl. No. 12/275,380, filed Nov. 21, 2008.
European Search Report dated Apr. 18, 2013 from corresponding European Patent Application No. 12197183.2.
Japanese Notification of Reasons for Refusal dated Nov. 8, 2016 in corresponding Japanese Application No. 2012-273212.

* cited by examiner

MONITORING AND TRACKING BIPOLAR ABLATION

BACKGROUND OF THE INVENTION

Field of the Invention

This invention relates to invasive medical devices. More particularly, this invention relates to ablation of tissue using such devices.

2. Description of the Related Art

Ablation of body tissue using electrical energy is known in the art. The ablation is typically performed by applying alternating currents, for example radiofrequency energy, to electrodes, at a sufficient power to destroy target tissue. Typically, the electrodes are mounted on the distal tip of a catheter, which is inserted into a subject. The distal tip may be tracked in a number of different ways known in the art, for example by measuring magnetic fields generated at the distal tip by coils external to the subject. The catheter may be provided with unipolar or bipolar ablation electrodes.

Kratoska, U.S. Patent Application Publication No. 20080275440 is directed to a method of providing feedback regarding the outcome of ablation therapy. A method is provided for obtaining feedback regarding the results of tissue ablation, the method comprising deploying one or more needles from a catheter into a target tissue, delivering energy via at least one of the one or more needles to ablate at least a portion of the target tissue to form a lesion, stopping energy delivery via the at least one of the one or more needles, and measuring a tissue property via at least one of the one or more needles after the energy delivery has been stopped. The measured tissue property may be temperature or impedance. Also, the measured tissue property may be used to determine a volume of the lesion formed by ablation therapy.

SUMMARY OF THE INVENTION

There is provided according to embodiments of the invention a method for treating abnormal cardiac electrical activity, which is carried out by providing a probe having first and second ablation electrodes disposed on a distal portion of the probe and a sensing electrode disposed between the first and second ablation electrodes, bringing the probe into contact with a target tissue in a heart of a subject, and applying energy through the first and second ablation electrodes to ablate the target tissue along an ablation path. The method is further carried out by while applying energy, monitoring cardiac electrical activity using the sensing electrode to detect the cardiac electrical activity, making an observation that the cardiac electrical activity is no longer detectable by the sensing electrode, and responsively to the observation terminating energy application.

According to another aspect of the method, the cardiac electrical activity is near-field activity.

According to yet another aspect of the method, there is a phase shift of 90° between an E field and an H field of the cardiac electrical activity.

According to still another aspect of the method, applying energy includes alternating between a bipolar mode of operation wherein the first and second ablation electrodes function as bipolar electrodes and a unipolar mode of operation wherein at least one of the first and second ablation electrodes functions as a unipolar electrode.

Yet another aspect of the method includes monitoring applying energy by graphically displaying a map of a portion of the heart that includes the target tissue and a progression of energy application along the ablation path.

According to an additional aspect of the method, applying energy also includes alternating between a bipolar mode of operation wherein the first and second ablation electrodes function as bipolar electrodes and a unipolar mode of operation wherein at least one of the first and second ablation electrodes functions as a unipolar electrode, and wherein monitoring cardiac electrical activity includes tagging the map to indicate first and second portions of the ablation path associated with the bipolar mode of operation and the unipolar mode of operation, respectively.

According to one aspect of the method, the probe has at least two sensing electrodes disposed between the first and second ablation electrodes.

There is further provided according to other embodiments of the invention apparatus for carrying out the above-described method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

System Description

Figure 1:
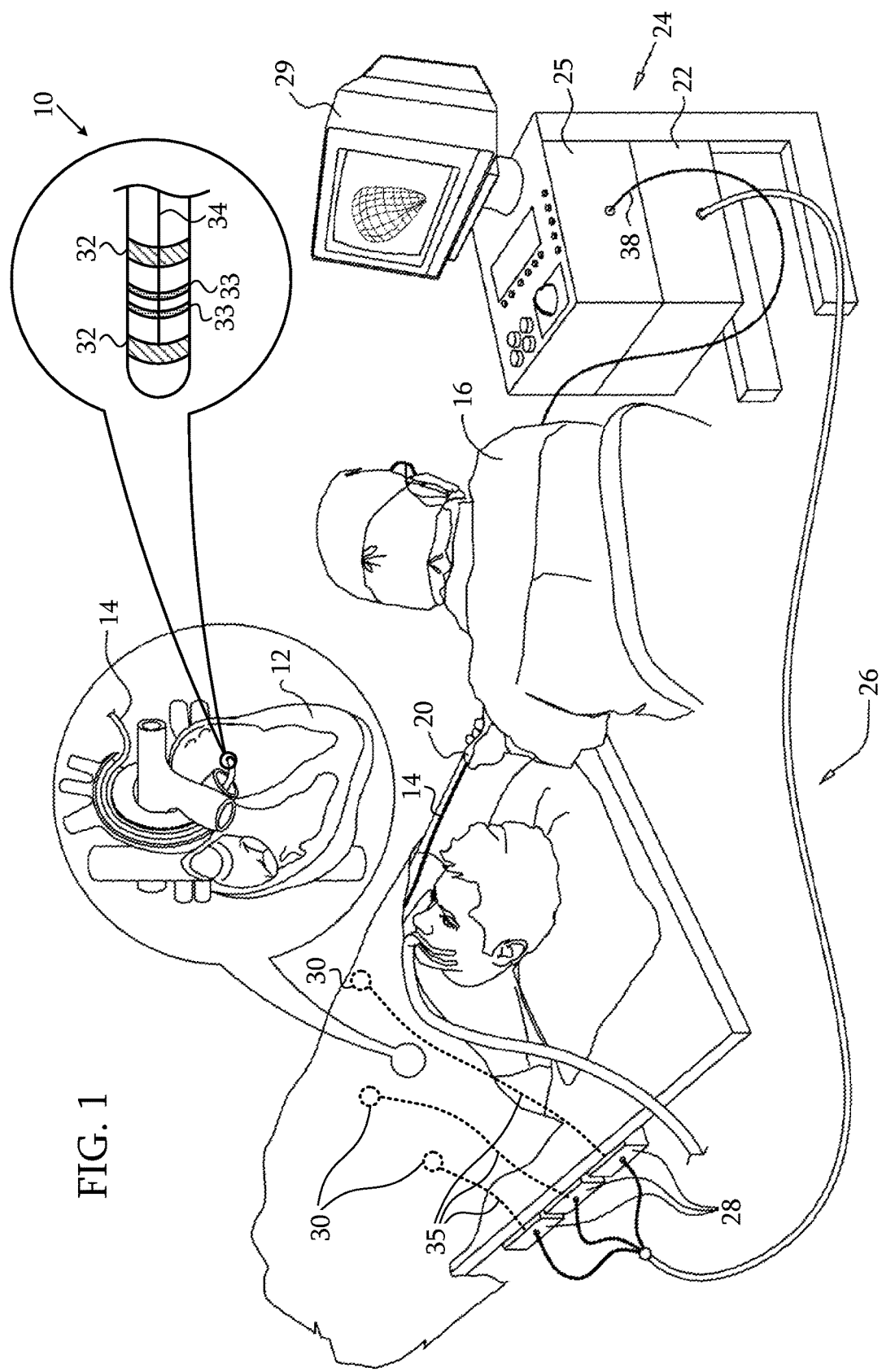
FIG. 1 is a pictorial illustration of a system for performing ablative procedures, which is constructed and operative in accordance with a disclosed embodiment of the invention.

Turning now to the drawings, reference is initially made to FIG. 1, which is a pictorial illustration of a system 10 for performing ablative procedures on a heart 12 of a living subject or patient, which is constructed and operative in accordance with a disclosed embodiment of the invention.

The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers, to mapping in sinus rhythm, and when to treat many different cardiac arrhythmias.

Unipolar ablation creates relatively deep lesions that are centered on the location of the ablation electrode, while bipolar ablation tends to create shallower, elongated lesions extending between a pair of bipolar electrodes. The nature and location of these bipolar lesions can create difficulty in lesion assessment and tracking.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34. During ablation the ablation electrodes 32 are typically operated in a bipolar configuration. However, one or both of them may be operated as unipolar electrodes using configuration circuitry for varying the mode of operation between a bipolar and a unipolar mode as required during an ablation.

Wire connections 35 link the console 24 with body surface electrodes 30 and other components of a positioning sub-system. The electrodes 32 and the body surface electrodes 30 may be used to measure tissue impedance measuring at the ablation site as taught in U.S. Pat. No. 7,536,218, issued to Govari et al., which is herein incorporated by reference. A temperature sensor 37, typically a thermocouple or thermistor, is mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning sub-system of the system 10 that measures location and orientation coordinates of the catheter 14.

In one embodiment, the positioning sub-system comprises a magnetic position tracking arrangement that determines the position and orientation of the catheter 14 by generating magnetic fields in a predefined working volume its vicinity and sensing these fields at the catheter using field generating coils 28.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning sub-system to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

The catheter 14 typically includes one or more pairs of ablation electrodes 32 as shown in FIG. 1, with one or more of the sensing electrodes 33 disposed between each pair of the ablation electrodes 32. Typically, the ablation electrodes 32 have a large area in order to effectively deliver RF power to the tissue, while the sensing electrodes 33 may be relatively smaller, as shown in the figure. In the ring electrodes shown in FIG. 1, the ablation electrodes 32 should be wider than the sensing electrodes 33.

Although the pictured embodiment includes two ring electrodes side-by-side, it is also possible to use a single sensing electrode or to use a single split ring to serve as a pair of sensing electrodes. The sensing electrodes 33 sense local electrical activity in the heart, and, with the aid of suitable detection and monitoring circuitry (not shown) in the console 24, track the progress of lesion formation by detecting a drop in the electrical amplitude. For this purpose, a pair of sensing electrodes is preferable, since it enables bipolar measurement of near-field electrical signals (having a phase shift of 90° between the E field and H field, so that no energy is transported and hence gives a more accurate indication of local electrical activity. Complete ablation is indicated by extinguishment of the local electrical activity. It is possible to dynamically reconfigure the ablation electrodes 32 to operate selectively in bipolar mode and unipolar mode according to the local requirements of the lesion required to be generated.

Ablation Monitoring

Figure 2:
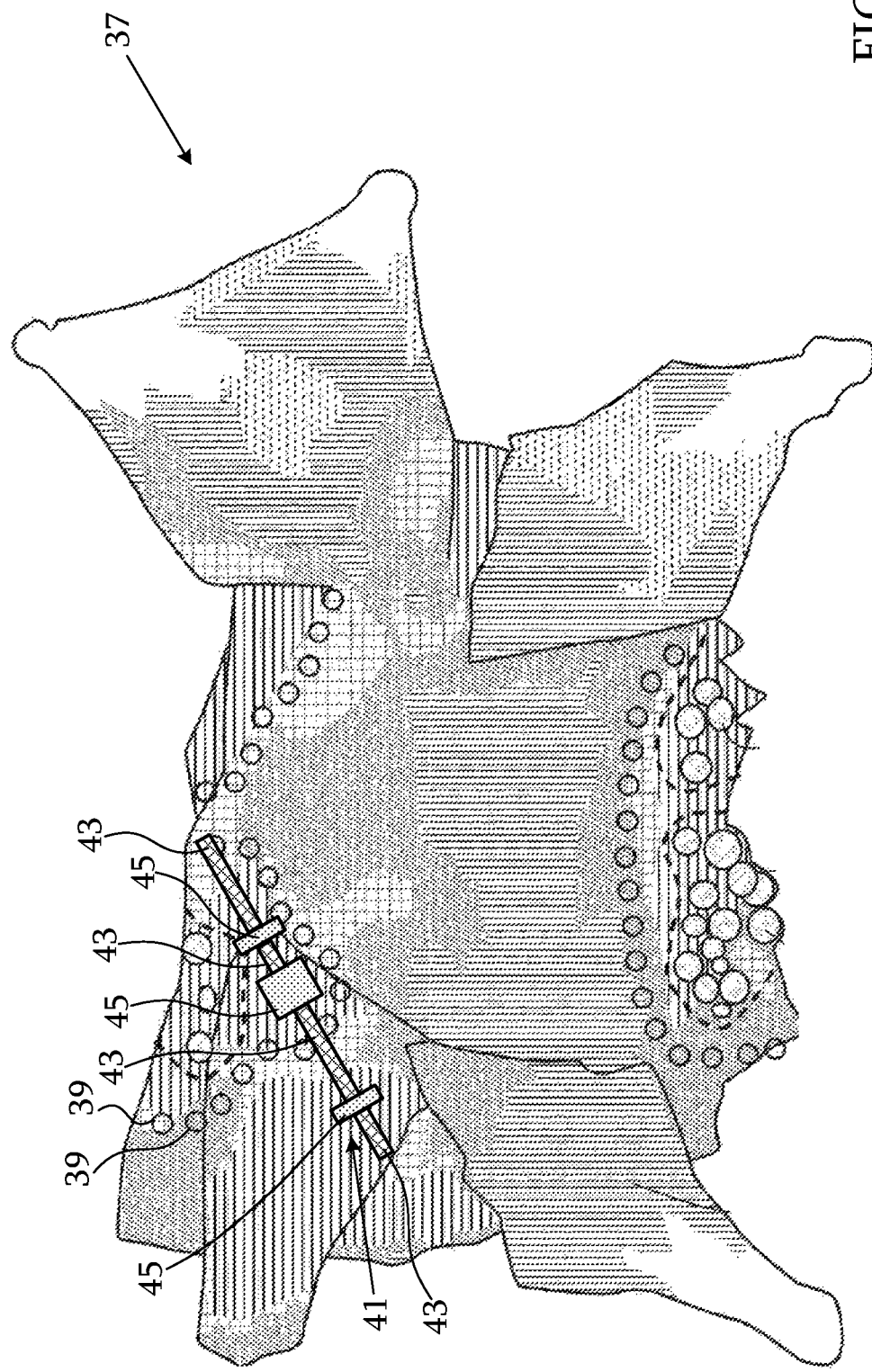
FIG. 2 is an electroanatomical map in the postero-anterior projection of a heart undergoing ablation according to an embodiment of the invention.

Bipolar ablation may optionally be tracked graphically as it proceeds along a path, so that the operator can readily determine when a line or annulus has been completely ablated. Reference is now made to FIG. 2, which is a prospective example of an electroanatomical map 37 in the posteroanterior projection of a heart undergoing ablation according to an embodiment of the invention. The above-noted CARTO 3 system is capable of producing such maps. In this example, regions containing ganglionated plexi are outlined by circles 39. These regions would guide the selection of a position and orientation of a lesion 41 to be established by ablation in order to treat an arrhythmia, for example an arrhythmia associated with complex fractionated atrial electrograms. Techniques for localizing and treating of such arrhythmias are taught in commonly assigned copending application Ser. No. 12/275380, which is herein incorporated by reference. Of course, many other arrhythmias and aberrant conduction paths may be treated according to the principles of the invention.

As ablation proceeds, the process is tracked and displayed on the map 37 as a series of connected tags, in which rectangles 43 having cross-hatched patterns represent intervals of bipolar ablation, and rectangles 45, generally oriented perpendicular to the rectangles 43 represent intervals of unipolar ablation. The lesion 41 appears linear; however this is not necessarily the case. Such lesions may be curvilinear, or even discontinuous. The rectangles 43 may be distinguished from the rectangles 45, for example by graphical techniques, e.g., color.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A medical apparatus, comprising:
   a probe defining a longitudinal axis and having a bipolar ablation element disposed on a distal portion of the probe, the bipolar ablation element consisting of first and second ablation electrodes concentrically disposed on the distal portion of the probe relative to the longitudinal axis and a dedicated sensing electrode concentrically disposed on the distal portion of the probe relative to the longitudinal axis and between the first and second ablation electrodes, the first and second ablation electrodes being configured to operate as a bipolar pair in a bipolar mode to deliver RF energy to ablate tissue and form a lesion that extends between the first and second ablation electrodes, the dedicated sensing electrode being separate and distinct from the first and second ablation electrode and configured to sense local electrical activity in the heart when the ablation electrodes are delivering RF energy;
   an ablation energy generator connected to the first and second ablation electrodes; and
   a monitor connected to the sensing electrode and operative to detect cardiac electrical activity via the sensing electrode when the probe is brought into contact with a target tissue in a heart of a subject, the monitor comprising monitoring circuitry configured to track the progress of lesion formation by detecting a drop in the electrical amplitude of the electrical activity and a graphical display operative for displaying a map of a portion of the heart that includes the target tissue and a progression of energy application along an ablation path.

2. The apparatus according to claim 1, wherein the cardiac electrical activity is near-field activity.

3. The apparatus according to claim 1, wherein there is a phase shift of 90° between an E field and an H field of the cardiac electrical activity.

4. The apparatus according to claim 1, further comprising configuration circuitry for configuring the first and second ablation electrodes to function in a bipolar mode of operation wherein the first and second ablation electrodes function as bipolar electrodes and in a unipolar mode of operation wherein at least one of the first and second ablation electrodes functions as a unipolar electrode.

5. The apparatus according to claim 4, wherein the monitor is operative for tagging the map to indicate first and second portions of the ablation path associated with the bipolar mode of operation and the unipolar mode of operation, respectively.

6. The apparatus according to claim 1, wherein the sensing electrode comprises at least two dedicated sensing electrodes disposed between the first and second ablation electrodes, the at least two dedicated sensing electrodes being configured to enable bipolar measurement of near-field electrical signals so that no energy is transported to the tissue.

7. The apparatus according to claim 1 wherein each of the ablation electrodes have a larger area than the sensing electrode.

8. The apparatus according to claim 7 wherein the ablation electrodes and sensing electrode are ring electrodes.

9. The apparatus according to claim 8 wherein each of the ablation electrodes are wider than the sensing electrode.

* * * * *